(12) United States Patent  
Vollkron et al.

(10) Patent No.: US 9,026,209 B2
(45) Date of Patent: May 5, 2015

(54) VENTRICULAR CARDIAC STIMULATOR

(75) Inventors: Michael Vollkron, Pressbaum (AT); Michael Lippert, Ansbach (DE)

(73) Assignee: Biotronik CRM Patent AG (CH)

( * ) Notice: Subject to any disclaimer, the term of this patent is extended or adjusted under 35 U.S.C. 154(b) by 770 days.

(21) Appl. No.: 12/830,750

(22) Filed: Jul. 6, 2010

(65) Prior Publication Data

US 2011/0029035 A1 Feb. 3, 2011

Related U.S. Application Data

(60) Provisional application No. 61/228,978, filed on Jul. 28, 2009.

(51) Int. Cl.
*A61N 1/368* (2006.01)
*A61N 1/362* (2006.01)

(52) U.S. Cl.
CPC ............. *A61N 1/3627* (2013.01); *A61N 1/3684* (2013.01); *A61N 1/3688* (2013.01)

(58) Field of Classification Search
CPC .. A61N 1/3627; A61N 1/3684; A61N 1/3688
USPC .................................................. 607/9, 15, 25
See application file for complete search history.

(56) References Cited

U.S. PATENT DOCUMENTS

| | | | |
|---|---|---|---|
| 6,748,267 B2 * | 6/2004 | Shekhar et al. | 607/4 |
| 7,113,823 B2 * | 9/2006 | Yonce et al. | 607/9 |
| 2004/0215257 A1 | 10/2004 | Van Oort et al. | |
| 2005/0125041 A1 * | 6/2005 | Min et al. | 607/9 |
| 2006/0224198 A1 | 10/2006 | Dong et al. | |
| 2008/0009909 A1 * | 1/2008 | Sathaye et al. | 607/9 |
| 2009/0125077 A1 | 5/2009 | Doerr et al. | |

FOREIGN PATENT DOCUMENTS

| | | |
|---|---|---|
| DE | 602 15 458 T2 | 8/2007 |
| EP | 2060299 A1 | 10/2008 |

OTHER PUBLICATIONS

European Search Report, EP 10168723.4-2305, Nov. 2, 2010.

* cited by examiner

*Primary Examiner* — Alyssa M Alter
(74) *Attorney, Agent, or Firm* — Craig A. Fieschko, Esq.; DeWitt Ross & Stevens S.C.

(57) ABSTRACT

An implantable cardiac stimulator includes at least one first sensing unit for detecting intrinsic cardiac activities of a first ventricle, at least one ventricular stimulation unit for stimulating a second ventricle, and a stimulation control unit connected to the first sensing unit. The stimulation unit processed output signals of the first sensing unit and generates control signals for the stimulation units. The stimulation control unit derives a current intrinsic RR interval from detected ventricular intrinsic cardiac activities R of the first ventricle, and to determine from the RR interval a delay interval Δ, which begins with a ventricular event of the first ventricle and at the end of which the stimulation control unit triggers a stimulation of the second ventricle (unless it is suppressed).

20 Claims, 4 Drawing Sheets

VENTRICULAR CARDIAC STIMULATOR

CROSS-REFERENCE TO RELATED APPLICATIONS

This application claims priority under 35 USC 119(e) to U.S. Provisional Patent Application 61/228,978 filed Jul. 28, 2009, the entirety of which is incorporated by reference herein.

FIELD OF THE INVENTION

The invention relates to an implantable cardiac stimulator (e.g., a cardiac pacemaker, an implantable cardioverter/defibrillator (ICD), or a combination of these devices), preferably one which is capable of stimulating both ventricles of the heart, for cardiac resynchronization therapy (CRT).

BACKGROUND OF THE INVENTION

A cardiac stimulator of the aforementioned type typically has at least one right-ventricular sensing unit and one right-ventricular stimulation unit, plus one left-ventricular sensing unit and one left-ventricular stimulation unit. These units are connected by electrode lines to electrodes situated at suitable locations in the heart during operation of the cardiac stimulator. A left-ventricular electrode line typically bears the electrodes for detecting electric potentials in, and delivering stimulation pulses to, the left ventricle of the heart. The left-ventricular electrode line is usually implanted through the coronary sinus of the heart, and therefore is also referred to as a coronary sinus electrode line, though it may instead be an epicardial or endocardial electrode line to the left ventricle. The electrodes for detecting electric potentials in, and delivering stimulation pulses to, the right ventricle are typically attached to a right-ventricular electrode line whose distal end is situated at the apex of the right ventricle. The electrode lines are typically connected at their proximal end to a cardiac stimulator via standardized plug connections.

Typical stimulation modes for a right-ventricular cardiac stimulator, e.g., VVI, VVD or DDD, are well-known. The same is also true regarding modes for delivery of stimulation pulses only in case of need (demand pacemaker modes), in which delivery of a stimulation pulse to a particular chamber of the heart is suppressed when an assigned sensing unit of the cardiac stimulator has detected an intrinsic pulse in the chamber during a corresponding escape interval. These known concepts may be implemented with the cardiac stimulator described here.

Automatic (non-stimulated) contractions of a particular cardiac chamber are also referred to as intrinsic events, sense events, or intrinsic cardiac activities. They may be detected in a known manner by corresponding sensing units, which are connected to a particular electrode for detecting myocardial potentials during operation. In order for a particular sensing unit to avoid impairment by a potential due to the delivery of a stimulation pulse, sensing units are typically designed so that they do not detect any events within a short blanking period following a stimulus. Delivery of a stimulation pulse is also known as a pace event.

In common cardiac resynchronization therapy methods, to correct a dys-synchronicity of the right and left ventricles, the ventricles are electrically stimulated in order to ensure a defined interventricular delay time (VV delay, or VVD). This is true even with intact AV conduction, i.e., with natural conduction of a stimulus triggering a contraction from the atrium to the ventricle over the AV node. This methodology foregoes a more efficient contraction of the intrinsically stimulable ventricle and the associated natural regulation of AV delay (which also reflects physical exertion, for example).

US Published Patent Appln. 2009/0125077 proposes a cardiac stimulator which can automatically switch between a plain right-ventricular stimulation mode and a biventricular stimulation mode of the aforementioned type.

SUMMARY OF THE INVENTION

An objective of the invention is to provide a cardiac stimulator that will allow efficient cardiac resynchronization therapy (CRT). The invention includes an implantable cardiac stimulator having at least one first sensing unit for detecting intrinsic cardiac activities of a first ventricle, which has an input that is or can be connected to a first electrode line. The first sensing unit is designed to analyze an electric input signal applied at its input, such that the sensing unit detects at least one signal feature that is typical of a contraction of the first ventricle and creates a corresponding output signal. Furthermore, the cardiac stimulator has at least one stimulation unit for stimulating a respective second ventricle of the heart, which has an output that is or can be connected to a second electrode line. The stimulation unit is designed to generate a ventricular stimulation pulse in response to a control signal and deliver it via the output. A stimulation control unit is connected to the first sensing unit and the stimulation unit and is designed to process output signals of the sensing unit and to generate control signals for the stimulation unit. The stimulation control unit is configured to derive a current intrinsic RR interval from the detected ventricular intrinsic cardiac activities R of the first ventricle, and to determine from the RR interval a delay interval $\Delta$. The delay interval $\Delta$ begins with a ventricular event of the first ventricle, and at its end, the stimulation control unit triggers stimulation of the second ventricle, unless it is inhibited.

In practice, the "first ventricle" noted above is usually the right ventricle, but it may also be the left ventricle (e.g., in the case of a right-leg block).

The invention is based on the finding that when a heart suitable for resynchronization has an intrinsic rhythm in one ventricle, resynchronization can be achieved only by stimulation in the other ventricle. As long as the control unit of the cardiac stimulator can detect an intrinsic rhythm in the first chamber of the heart (i.e., there is no AV block), the point in time of stimulation in the second chamber is determined according to the method described below. If there is no longer an intrinsic ventricular rhythm (e.g., AV block, sinus bradycardia), then resynchronization is preferably performed according to the traditional method (stimulation in both ventricles). For an intermittent AV block, automatic switching may be provided.

Resynchronization is achieved by a delay interval $\Delta$ (see FIG. 4) which is adapted beat-for-beat to the RR, the duration of the last intrinsic RR interval. The RR may optionally be calculated from preceding RR intervals, e.g., a current RR may be averaged (perhaps via a weighted average) or otherwise affected by one or more preceding RR intervals. The stimulation point in time in one of the two ventricles thus follows the respective variability of the heart rate and the intrinsic AV delay.

In practice, the second (asynchronous) ventricle should be stimulated such that it contracts simultaneously with the first (intrinsically stimulated) ventricle. This can be achieved by stimulation of the second ventricle a certain interval of time VVD before detection in the first ventricle (in the same cardiac cycle). To define this point in time, stimulation is performed in the second ventricle after the interval of time $\Delta$=RR−VVD has elapsed, starting from the intrinsic stimulation in the preceding cardiac cycle.

To this end, it is also necessary to differentiate stimulation of the first ventricle by atrioventricular conduction (via the AV node) from interventricular conduction starting from the second ventricle (stimulated previously).

The stimulation control unit is preferably designed to suppress (inhibit) stimulation in a particular ventricle when an intrinsic event (intrinsic ventricular activity) is detected there.

The stimulation control unit is preferably designed to stimulate the second ventricle immediately (tracking) when there is a positive VVD in the case of intrinsic detection in the first ventricle before the calculated stimulation time for the second ventricle.

The stimulation control unit is preferably also designed to determine the delay interval $\Delta$, taking into account a predetermined interventricular delay time VVD. Synchronization may be refined with the help of a hemodynamic replacement variable, e.g., by adaptation of the parameter VVD [ms]. This parameter VVD indicates by how much the second ventricle (to be resynchronized) is to be stimulated before the next expected intrinsic stimulation in the first ventricle.

VVD may therefore have a predetermined default value, which is stored in a memory of the cardiac stimulator. For example, the interventricular delay VVD may be determined during consultation with one's physicians.

The interventricular delay time VVD may be adjusted manually to reach a hemodynamic optimum, which is derived, e.g., from intracardiac impedance, pressure sensors, imaging methods or the like.

If a negative VVD (which corresponds to stimulation of the second ventricle only after detection in the first ventricle) is necessary and/or if it is obtained as an optimum value, the second ventricle is stimulated with a delay of −VVD after detection in the first ventricle of the same cardiac cycle. No RR value is needed in this case.

For the case when no intrinsic stimulation is detected in the first ventricle, because it falls in the blanking period after the ventricular stimulation and therefore a direct determination of the delay interval $\Delta$ is impossible, the stimulation control unit is designed to:

(1) Determine the delay interval $\Delta$ as the difference between the last intrinsic stimulation and the middle of the blanking interval;
(2) Alter the delay interval $\Delta$ by a correction term +delta or −delta (delta being so small that no significant influence on hemodynamics is expected, e.g., 20 ms), and to check on whether an intrinsic stimulation can be detected. If this is the case with one of the values, this correction term is retained.
(3) If this is not successful, stimulation of the second ventricle is suppressed for one or more heartbeats. If intrinsic events then occur in the first ventricle, the intrinsic RR interval and a new delay interval $\Delta$ are determined. If no intrinsic event occurs in the first ventricle (e.g., AV block or sinus bradycardia, both leading to stimulation in the first ventricle), then there is an automatic switch to normal biventricular CRT stimulation because of a lack of intrinsic conduction.

Furthermore, the stimulation control unit is preferably designed to detect direct conduction from the second ventricle to the first ventricle by altering the delay interval $\Delta$ for one or more cycles by a period $\tau$ at regular intervals, and determining the resulting change in the RR interval. If RR also changes by $\tau$ in the same direction, the stimulation control unit detects a direct conduction and reduces the delay interval VVD. As an alternative, the pacing in the second ventricle (starting from the unwanted conduction) may be suppressed for one or more beats.

In a preferred version of the invention, the implantable cardiac stimulator allows sensing in both ventricles and offers the possibility of stimulation in at least one of the two ventricles.

Furthermore, it is preferred to have the blanking time after a ventricular stimulus be as short as possible in order to be able to determine the delay interval $\Delta$ with adequate precision even in the case of almost simultaneous sense events and pace events.

The invention provides a number of advantages, including:
(a) Utilizing the natural stimulus conduction in the right ventricle leads to a more efficient contraction.
(b) The natural adaptation of the AV delay time (AV delay) to various load states is utilized.
(c) The invention offers a simple concept for continuous adaptation of the VV delay with intact AV conduction.
(d) In a preferred version, the invention allows the detection of conduction from the left ventricle to the right ventricle.
(e) The invention allows lower energy consumption than traditional biventricular cardiac stimulators by reducing the frequency of RV stimulation.
(d) The invention offers a suggested approach to the clinical question: why should the right ventricle be artificially stimulated when conduction is intact?
(e) The invention also extends to automatic AV/VV optimization. If the cardiac stimulator is designed to automatically determine an optimal AV delay (an optimal atrioventricular delay time), this may lead to an optimal AVD setting, which results in an intrinsic stimulation in the first ventricle. In this case, it is possible to switch seamlessly to the method presented here.

BRIEF DESCRIPTION OF THE DRAWINGS

An exemplary version of the invention will now be explained in greater detail with reference to the accompanying figures, in which.

DETAILED DESCRIPTION OF THE INVENTION

Figure 1:
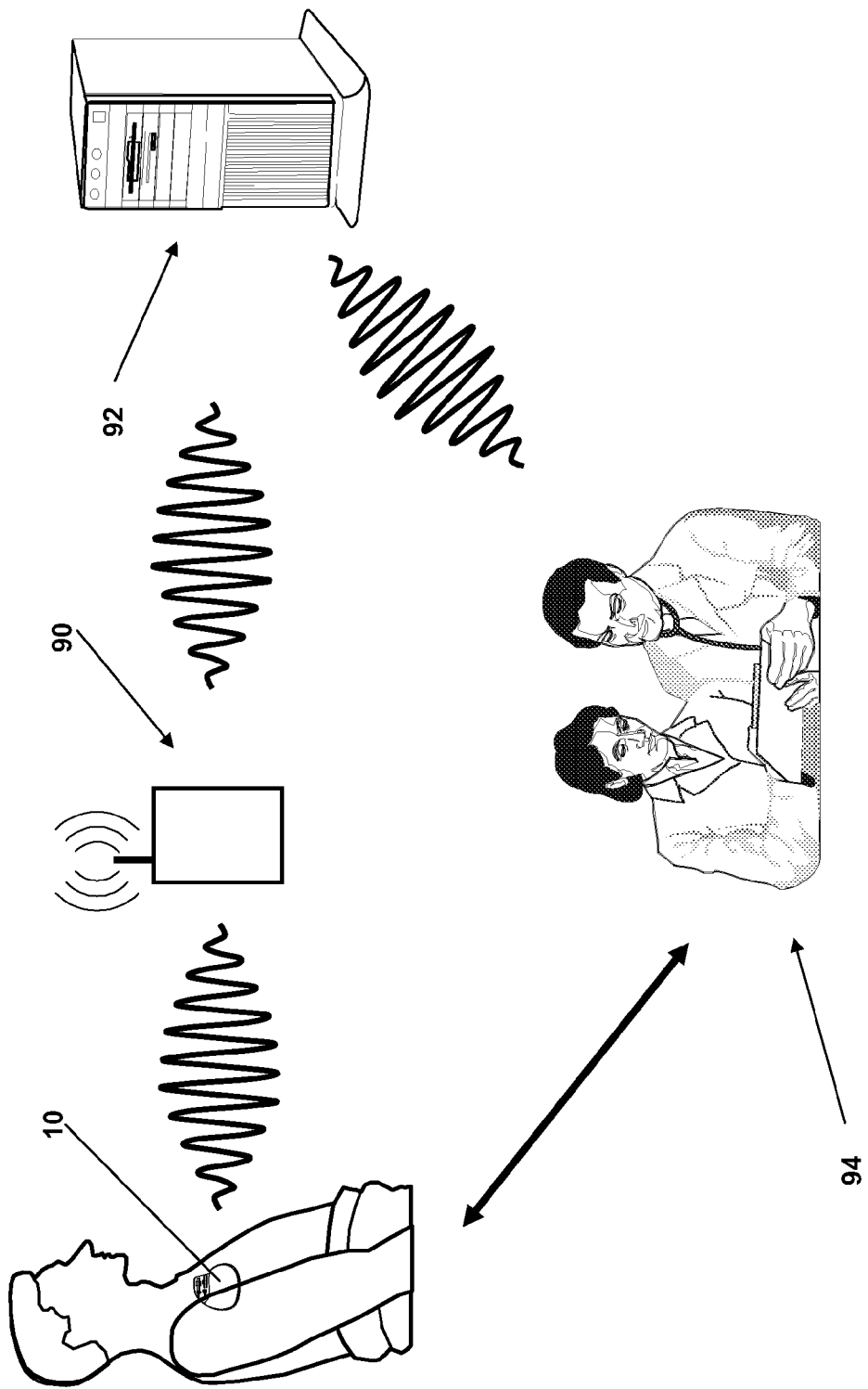
FIG. 1: shows a schematic diagram of a cardiac therapy system.

FIG. 1 shows a cardiac treatment system including an implanted cardiac pacemaker 10, an external device (patient device) 90, and a service center 92 represented symbolically by a server. The implantable cardiac stimulator 10 has a telemetry unit allowing wireless exchange of data with the external device 90. The external device 90 is connected (e.g., by wire) to the service center 92, for example, so that data can be exchanged between the service center 92 and the implantable cardiac stimulator 10 via the external device 90 as a relay station. Physicians 94 can then access data received by the service center 92 from the implantable cardiac stimulator 10.

Figure 2:
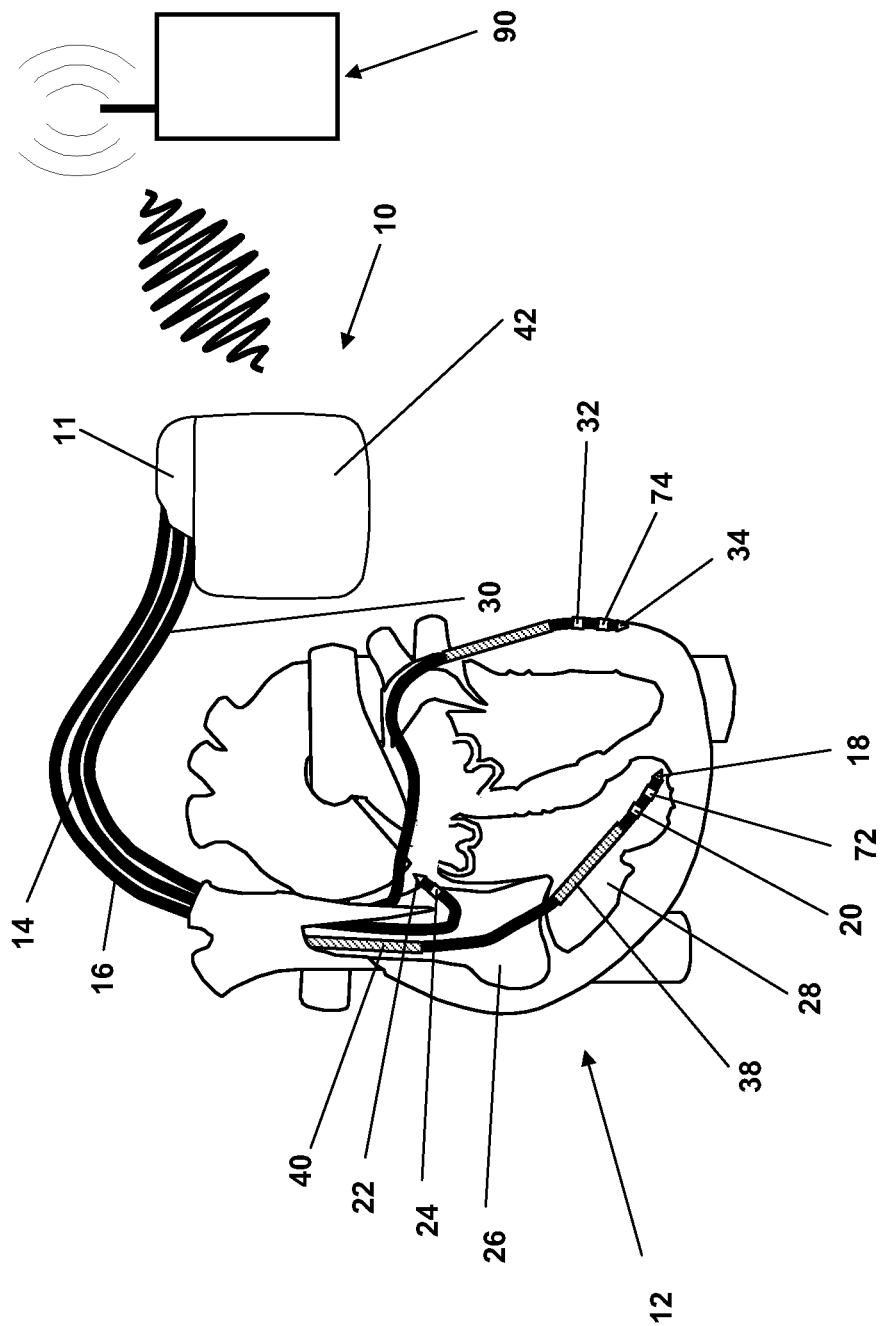
FIG. 2: shows a diagram of a cardiac stimulator with connected electrodes arranged in the heart.

FIG. 2 shows the implantable cardiac stimulator 10 in the form of a triple-chamber cardiac pacemaker/cardioverter/defibrillator with electrode lines 14, 16 and 30 connected thereto in combination with a heart 12, and in the vicinity of the external device 90. The electrode lines 14, 16 and 30 are electrically connected to contact bushings in a header (connecting housing) 11 of the cardiac stimulator 10 via standardized plug connections. In this way, the electrode lines 14, 16 and 30 are also connected to electronic components in the interior of a hermetically sealed metal housing 42 of the cardiac stimulator 10. These components are presented schematically in greater detail below, and control the functionality of the cardiac stimulator 10.

The electrode line 14 is a right-atrial electrode line and has an atrial tip electrode (RA tip) 22 on its distal end and an atrial ring electrode (RA ring) 24 situated a short distance from the RA tip 22. Both electrodes are placed in the right atrium 26 of the heart 12.

The electrode line 16 is a right-ventricular electrode line and has a right-ventricular tip electrode (RV tip) 18 on its distal end and has a right-ventricular ring electrode (RV ring) 20 situated nearby. Both electrodes are arranged at the apex of the right ventricle 28 of the heart 12. The right-ventricular electrode line 16 also includes a right-ventricular shock coil (RV shock) 38 as a large-area electrode for delivering defibrillation shocks. Another shock coil 40 is arranged in the superior vena cava, and is also referred to below as an SVC shock electrode 40.

The electrode line 30 is a left-ventricular electrode line having a distal left-ventricular tip electrode (LV tip) 34, a nearby left-ventricular ring electrode (LV ring) 32. (A left-ventricular shock coil is also shown in FIG. 2 on the left-ventricular electrode line 30 for delivering defibrillation shocks to the left ventricle, but this is not labeled nor discussed further.) The left-ventricular electrode line 30 is guided out of the right atrium 26 of the heart through the coronary sinus into a branching lateral vein, and therefore is also referred to as the coronary sinus electrode line 30 or CS electrode line 30.

Figure 3:
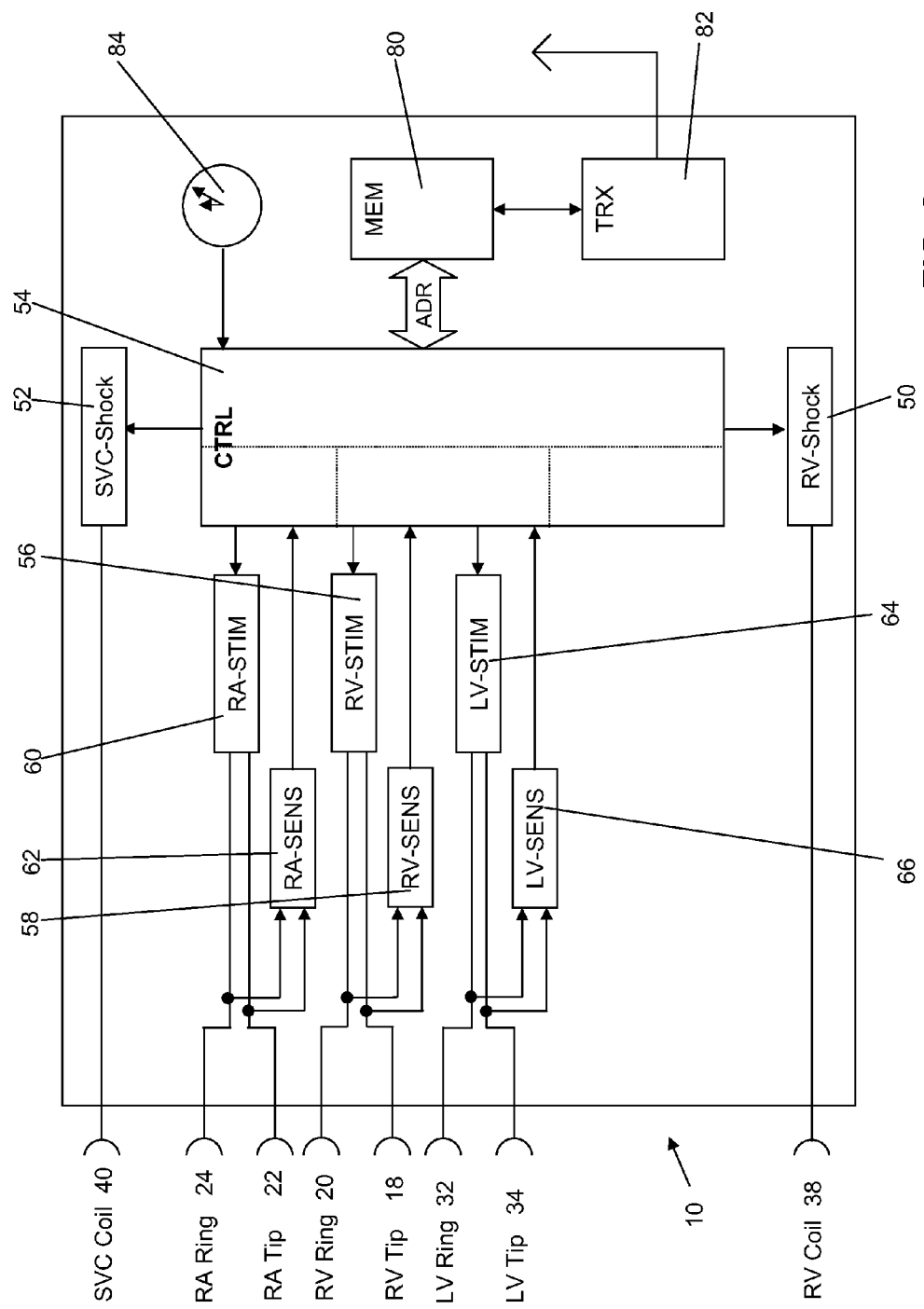
FIG. 3: shows a schematic block diagram of a cardiac stimulator.

FIG. 3 schematically illustrates the foregoing components of the cardiac stimulator 10. The electric terminals for the various electrodes 18, 20, 22, 24, 32, 34, 38 and 40 are shown on the left side. The shock electrodes 38 and 40 are each connected to a right-ventricular shock pulse generator RV-Shock 50 and/or an SVC shock pulse generator SVC-Shock 52. Both of the shock generators 50 and 52 are connected to a stimulation control unit 54, which controls the two shock pulse generators 50 and 52 as needed to generate and deliver a defibrillation shock. A similar shock pulse generator can be implemented for the left ventricular shock electrode (not labeled in FIG. 1).

The terminal for the right-ventricular tip electrode RV tip 18 and the terminal for the right-ventricular ring electrode RV ring 20 are both connected to a right-ventricular stimulation unit 56 and a right-ventricular sensing unit 58. Both the right-ventricular stimulation unit 56 and the right-ventricular sensing unit 58 are connected to the stimulation control unit 54.

The right-ventricular stimulation unit 56 is designed to generate a right-ventricular stimulation pulse in response to a triggering signal of the stimulation control unit 54 and to subsequently deliver the stimulation pulse to the right-ventricular tip electrode 22 and the right-ventricular ring electrode 20. Alternatively, it is also possible for the housing 42 of the cardiac stimulator 10 to form a neutral electrode and for the right-ventricular stimulation unit 56 to be connected to the terminal for the right-ventricular ring electrode 18, with the housing 42 defining another electrode for delivering a stimulation pulse. A right-ventricular stimulation pulse differs from a defibrillation shock in that the stimulation pulse has a much lower pulse intensity, so it does not stimulate all the cardiac tissue (myocardium) of a heart chamber simultaneously like a defibrillation shock, but instead stimulates only the myocardial cells in the immediate vicinity of the right-ventricular tip electrode 18. This stimulation then propagates through natural stimulus conduction over the entire ventricle and thus ensures a stimulated contraction of the ventricle.

The right-ventricular sensing unit 58 is designed to first amplify and filter the electric potentials applied to the terminal for the right-ventricular ring electrode RV ring 20 and the right-ventricular tip electrode RV tip 18 through an input amplifier (not shown). In addition, the right-ventricular sensing unit 58 is designed to analyze the characteristics of the electric signals applied at its inputs, so that the right-ventricular sensing unit 58 automatically detects an intrinsic (i.e., natural or independent contraction) of the right ventricle. This may take place, for example, by comparing the characteristics of the signal applied at the inputs of the right-ventricular sensing unit 58 with a threshold value. The greatest amplitude of the signal in the form of the so-called R wave is typically characteristic of a natural contraction of the right ventricle, which can be detected by threshold value comparison. The right-ventricular sensing unit 58 then delivers a corresponding output signal indicating a natural contraction of the right ventricle to the stimulation control unit 54.

Similarly, the terminal for the right-atrial tip electrode 22 and the terminal for the right-atrial ring electrode 24 are connected to a right-atrial stimulation unit 60 and also to a right-atrial sensing unit 62, each being in turn connected to the stimulation control unit 54. The right-atrial stimulation unit 60 is designed to generate stimulation pulses having a sufficient intensity to stimulate the right-atrial myocardium. The right-atrial stimulation pulses may have a different pulse intensity than the right-ventricular stimulation pulses. The right-atrial sensing unit 62 is designed to detect a so-called P wave from the differential signal applied at its input, said P wave being characteristic of an intrinsic (natural) contraction of the right atrium. If the right-atrial sensing unit 62 detects a corresponding P wave, it generates an output signal and sends it to the stimulation control unit 54, identifying a natural contraction of the right atrium.

In the same way, the terminal for the left-ventricular tip electrode LV tip 34 and the terminal for the left-ventricular ring electrode LV ring 32 are each connected to a left-ventricular stimulation unit 64 and a left-ventricular sensing unit 66. The left-ventricular stimulation unit 64 and the left-ventricular sensing unit 66 are likewise connected to the stimulation control unit 54. Both of them function like the stimulation units 56 and 60 and the sensing units 58 and 62 already described above.

In addition, the cardiac stimulator 10 includes a memory unit 80, which is connected to the stimulation control unit 54 and makes it possible to store signals generated or analyzed by the stimulation control unit 54. The memory unit 80 may also or alternatively be used to store control programs for the stimulation control unit 54 in a modifiable form. Most preferably, the memory unit 80 stores values of the most recent intrinsic RR intervals plus at least one value for an interventricular delay time VVD.

Furthermore, the stimulation control unit 54 is connected to a timer 84, which enables the stimulation control unit 54 to determine matter such as points in time and intervals of time.

The memory unit 80 is connected to a telemetry unit 82, which makes it possible to wirelessly transmit data stored in the memory unit 80 to the external device 100, or to transmit programming commands from the external device 100 to the cardiac stimulator 10 and store them in the memory unit 80.

As a triple-chamber cardiac stimulator/cardioverter/defibrillator, the cardiac stimulator 10 is capable of stimulating the right atrium, the right ventricle and the left ventricle or just one or two of these cardiac chambers in a known manner. This includes in particular stimulation of the respective cardiac chamber in demand mode, in which stimulation pulses are delivered to the respective cardiac chamber only when no intrinsic contraction of the respective cardiac chamber is detected by the respective sensing unit in a preceding respective escape interval. The cardiac pacemaker is thus capable of performing the known right-ventricular stimulation modes such as VVI, VVD or DDD.

For the timing of the stimulation pulses in the biventricular stimulation mode in which both ventricles of a heart are stimulated, an interventricular delay time (VV interval; VVD) is particularly important: this is the time by which a right stimulation pulse and a left stimulation pulse follow one another, if they are not inhibited in demand mode. This time may be less than 0, so the left stimulation pulse trails behind the right stimulation pulse. The interventricular delay time may be 0, which means that a right-ventricular stimulation pulse and a left-ventricular stimulation pulse are delivered simultaneously by simultaneous triggering of the right-ventricular stimulation unit 56 and the left-ventricular stimulation unit 64. The interventricular delay time may also be greater than 0, which means that a left-ventricular stimulation pulse is delivered before the delivery of the respective right-ventricular stimulation pulse.

The stimulation control unit 54 is designed to achieve a resynchronization of the right and left ventricles using at least one electrode in both the right and left ventricles. Stimulation in one of the two ventricles is suppressed by the stimulation control unit 54 when the respective sensing unit detects an intrinsic event there.

For resynchronization, the stimulation control unit 54 determines a delay interval $\Delta$ (see FIG. 4) which is adapted beat-for-beat to the duration of the last intrinsic RR interval. An optimization is performed here with the help of a hemodynamic replacement variable, for example, through the adaptation of a parameter VVD [ms]. This parameter VVD corresponds to an interventricular delay time and indicates by how much the ventricle to be resynchronized is to be stimulated before the next expected intrinsic stimulation.

The stimulation point in time in one of the two ventricles thus follows the respective variability of the heart rate and the intrinsic AV delay.

A suitable value for VVD is stored in the memory 80. It may be determined by a physician during a consultation, for example. VVD is varied to search for a hemodynamic optimum derived from intracardiac impedance, pressure sensors, imaging methods or the like, for example.

For the case when an intrinsic stimulation of the right ventricle is not detected because it falls in the blanking time after the ventricular stimulation and therefore a direct determination of the delay interval $\Delta$ is impossible, the stimulation control unit 54 determines the delay interval $\Delta$ as the difference between the last intrinsic stimulation and the middle of the blanking interval.

If that is not successful, the stimulation control unit 54 suppresses stimulation of the left ventricle for one heartbeat to measure the intrinsic RR and determine from that a new delay interval $\Delta$.

The stimulation control unit 54 is also designed to detect direct conduction from the left ventricle to the right ventricle (or vice versa) at regular intervals by reducing the delay interval $\Delta$ by $\tau$ for one or more cardiac cycles, and measuring the resulting change in the RR interval. If the RR also changes by $\tau$, then there is probably direct conduction. In this case, the stored value for the interventricular delay time VVD is reduced.

Figure 4:
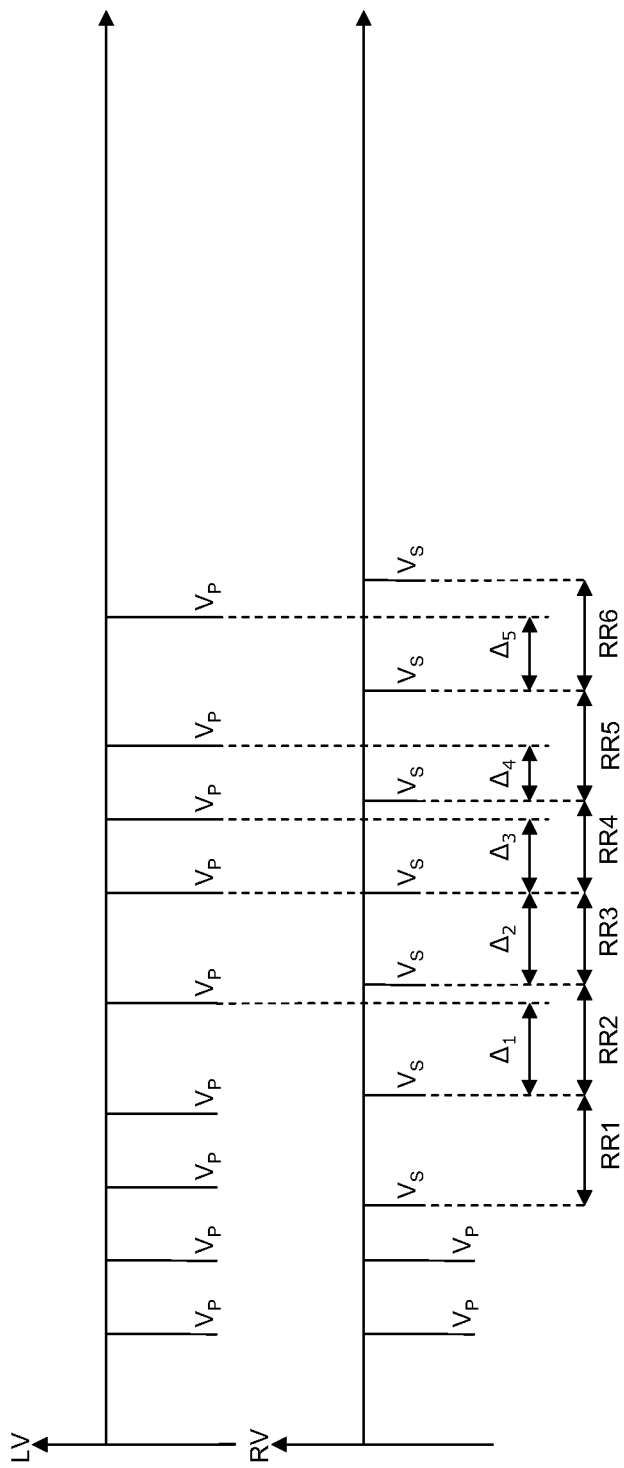
FIG. 4: shows an exemplary diagram of the chronological sequence of stimulation.

FIG. 4 shows an example of stimulation of the left ventricle with intermittent intact natural contraction of the right ventricle. Left-ventricular events are shown in the upper part of the figure, while right-ventricular events are shown in the lower part; stimulated (paced) events are labeled as Vp and intrinsic (sensed) events are labeled as Vs.

The stimulation control unit 54 uses the period of two successive intrinsic right- or left-ventricular contractions, detected by the respective sensing unit 58 or 66, for determination of an optimal delay interval $\Delta$ between a right-ventricular event and a left-ventricular pace event, i.e., the point in time at which a left-ventricular stimulation pulse is to be delivered. The first intrinsic RR interval RR1 is used together with a stored value for the interventricular delay time VVD for determining the first delay interval $\Delta_1$:

$$\Delta_1 = RR1 - VVD [ms]$$

By analogy, the next delay interval $\Delta_2$ is determined from the next intrinsic RR interval RR1 and with this, the point in time of the next left-ventricular stimulation pulse is determined:

$$\Delta_2 = RR2 - VVD [ms]$$

In the selected example, stimulation of the left ventricle takes place simultaneously with the right intrinsic stimulation because the heart rate (HR) has increased. The next stimulation in the left ventricle, following the higher HR, is accordingly stimulated sooner:

$$\Delta_3 = RR3 - VVD [ms]$$

In the example, the next intrinsic R interval is again longer because the heart rate has slowed. Therefore, the delay interval $\Delta_4$ between the next intrinsic event and the stimulation of the left ventricle is automatically longer:

$$\Delta_4 = RR4 - VVD [ms]$$

With the formation of the next delay interval $\Delta_5$ the adaptation to the delayed heart rate is concluded:

$$\Delta_5 = RR5 - VVD [ms]$$

It will be apparent to those skilled in the art that numerous modifications and variations of the described examples and versions are possible in light of the foregoing discussion. The disclosed examples and versions are presented for purposes of illustration only, and this patent extends to cover all alternative versions of the invention that fall literally within the scope of the claims below, as well as all equivalents of the claimed inventions.

What is claimed is:

1. An implantable cardiac stimulator including:
   a. a ventricular sensing unit:
      (1) having a ventricular sensing unit input which is or can be connected to a first electrode line, and
      (2) configured to:
         (a) detect intrinsic contractions of a first ventricle from electric input signals received at the ventricular sensing unit input, and
         (b) generate corresponding first ventricular output signals therefrom;
   b. a ventricular stimulation unit:
      (1) having a ventricular stimulation unit output which is or can be connected to a second electrode line, and
      (2) configured to:
         (a) generate a ventricular stimulation pulse in response to a control signal, and
         (b) deliver the ventricular stimulation pulse to a second ventricle via the ventricular stimulation unit output;

c. a stimulation control unit:
  (1) connected to the ventricular sensing unit and the ventricular stimulation unit, and
  (2) configured to:
    (a) receive the first ventricular output signals of the ventricular sensing unit,
    (b) determine a current intrinsic ventricular interval RR from the first ventricular output signals, and
    (c) determine from the interval RR a delay interval Δ which:
      (i) begins with an intrinsic contraction of the first ventricle, and
      (ii) at the end of which the stimulation control unit generates the control signal for the ventricular stimulation unit, thereby triggering the delivery of the ventricular stimulation pulse to the second ventricle via the ventricular stimulation unit output,
    wherein, if an intrinsic contraction of the first ventricle falls within a blanking interval occurring about the stimulation of the second ventricle, the stimulation control unit:
      A. defines the delay interval Δ as the difference between:
        I. the last intrinsic contraction of the first ventricle and
        II. a set time within the blanking interval,
      B. suppresses generation of the ventricular stimulation pulse for one cardiac cycle,
      C. determines the current intrinsic ventricular interval RR, and
      D. defines a new delay interval Δ from the current intrinsic ventricular interval RR.

2. The cardiac stimulator of claim 1 wherein the delay interval Δ is calculated as:

$$\Delta = RR - VVD$$

wherein VVD is an interventricular delay time.

3. The cardiac stimulator of claim 2 wherein:
  a. the cardiac stimulator is configured to determine an atrioventricular delay time between a right-atrial event and a right-ventricular event, and
  b. the stimulation control unit is configured to define the interventricular delay time VVD in dependence on the atrioventricular delay time determined by the cardiac stimulator.

4. The cardiac stimulator of claim 2 wherein the stimulation control unit is configured to detect a direct conduction between the first and second ventricles by:
  a. altering the delay interval Δ by an interval τ for one or more cardiac cycles, and
  b. if a resulting change in the RR interval is detected, thereby indicating a direct conduction, reducing the value of the interventricular delay time VVD.

5. The cardiac stimulator of claim 1 wherein the current intrinsic ventricular interval RR is defined by one or more preceding intrinsic ventricular RR intervals.

6. The cardiac stimulator of claim 1 wherein the set time occurs at the middle of the blanking interval.

7. The cardiac stimulator of claim 1 wherein if, after generation of the ventricular stimulation pulse is suppressed for one cardiac cycle, no intrinsic contraction of the first ventricle is detected by the ventricular sensing unit, the delay interval Δ is reduced until an intrinsic contraction of the first ventricle is detected.

8. An implantable cardiac stimulator including:
  a. a ventricular sensing unit for detecting intrinsic cardiac activities of a first ventricle, the ventricular sensing unit:
    (1) having a ventricular sensing unit input which is or can be connected to a first electrode line, and
    (2) configured to analyze an electric input signal applied at the ventricular sensing unit input, such that the ventricular sensing unit:
      (a) detects at least one signal feature typical of a contraction of the first ventricle, and
      (b) generates a corresponding first ventricular output signal;
  b. a ventricular stimulation unit for stimulating a second ventricle:
    (1) having a ventricular stimulation unit output which is or can be connected to a second electrode line, and
    (2) configured to:
      (a) generate a ventricular stimulation pulse in response to a control signal, and
      (b) deliver the ventricular stimulation pulse via the ventricular stimulation unit output, and
  c. a stimulation control unit:
    (1) connected to the ventricular sensing unit and the ventricular stimulation unit, and
    (2) configured to:
      (a) process the first ventricular output signal of the ventricular sensing unit,
      (b) generate the control signal for the ventricular stimulation unit,
      (c) determine a current intrinsic RR interval from detected intrinsic ventricular cardiac activities R of the first ventricle, and
      (d) determine from the RR interval a delay interval Δ which:
        (i) begins with a ventricular event of the first ventricle, and
        (ii) at the end of which the stimulation control unit triggers a stimulation of the second ventricle,
      wherein, if an intrinsic stimulation is not detected for the first ventricle because it falls in a blanking interval after stimulation of the second ventricle, the stimulation control unit is further configured to:
        A. determine the delay interval Δ as the difference between the last intrinsic stimulation of the first ventricle and a set time occurring within the blanking interval,
        B. suppress stimulation of the second ventricle for one cardiac cycle,
        C. determine the intrinsic RR interval,
        D. determine from the intrinsic RR interval a new delay interval Δ, and
        R. reduce the delay interval Δ until an intrinsic stimulation of the first ventricle can again be detected.

9. The cardiac stimulator of claim 8 wherein:
  a. the ventricular sensing unit is a right-ventricular sensing unit:
    (1) having a right-ventricular sensing unit input which is or can be connected to a right-ventricular electrode line, and
    (2) configured to analyze an electric input signal applied at the right-ventricular sensing unit input, such that the right-ventricular sensing unit:
      (a) detects at least one signal feature typical of a contraction of a right ventricle, and
      (b) generates a corresponding right-ventricular output signal;
  b. the first stimulation unit is a left-ventricular stimulation unit:

(1) having a left-ventricular stimulation unit output which is or can be connected to a left-ventricular electrode line, and
(2) configured to:
(a) generate a left-ventricular stimulation pulse in response to the control signal, and
(b) deliver the left-ventricular stimulation pulse via the left-ventricular stimulation unit output.

10. The cardiac stimulator of claim 8 wherein:
a. the ventricular sensing unit is a left-ventricular sensing unit:
(1) having a left-ventricular sensing unit input which is or can be connected to a left-ventricular electrode line, and
(2) configured to analyze an electric input signal applied at the left-ventricular sensing unit input, such that the left-ventricular sensing unit:
(a) detects at least one signal feature typical of a contraction of a left ventricle, and
(b) generates a corresponding left-ventricular output signal;
b. the first stimulation unit is a right-ventricular stimulation unit:
(1) having a right-ventricular stimulation unit output which is or can be connected to a right-ventricular electrode line, and
(2) configured to:
(a) generate a right-ventricular stimulation pulse in response to the control signal, and
(b) deliver the right-ventricular stimulation pulse via the right-ventricular stimulation unit output.

11. The cardiac stimulator of claim 8 wherein the cardiac stimulator includes:
a. two ventricular sensing units, one being a right-ventricular sensing unit and the other being a left-ventricular sensing unit; and
b. two ventricular stimulation units, one being a right-ventricular stimulation unit and the other being a left-ventricular stimulation unit.

12. The cardiac stimulator of claim 8 wherein the stimulation control unit is configured to determine the delay interval $\Delta$ as:

$$\Delta = RR - VVD$$

wherein VVD is an interventricular delay time.

13. The cardiac stimulator of claim 12 wherein:
a. the cardiac stimulator is configured to automatically determine an optimal atrioventricular delay time between a right-atrial event and a right-ventricular event, and
b. the stimulation control unit is configured to define the interventricular delay time VVD in dependence on the atrioventricular delay time determined by the cardiac stimulator.

14. The cardiac stimulator of claim 8 wherein the RR interval is defined by one or more preceding RR intervals.

15. The cardiac stimulator of claim 14 wherein the stimulation control unit is configured to:
a. change the delay interval $\Delta$ by $\tau$ for one or more cardiac cycles,
b. determine a resulting change in the RR interval, and when the RR interval is also changed by $\tau$, reduce the interventricular delay time VVD.

16. The cardiac stimulator of claim 8 wherein if, after stimulation of the second ventricle is suppressed for one cardiac cycle, no intrinsic contraction of the first ventricle is detected by the ventricular sensing unit, the delay interval 66 is reduced until an intrinsic contraction of the first ventricle is detected.

17. A cardiac stimulation method including the steps of:
a. detecting intrinsic contractions of a first ventricle;
b. defining a current intrinsic ventricular interval RR equal to the time between a current intrinsic contraction of the first ventricle and a last intrinsic contraction of the first ventricle;
c. trigger a stimulation of a second ventricle after a delay interval $\Delta$ measured from the subsequent intrinsic contraction of the first ventricle, wherein:
(1) $\Delta = RR - VVD$, and
(2) VVD is an interventricular delay time,
d. if an intrinsic contraction of the first ventricle occurs within a blanking interval after stimulation of the second ventricle:
(1) define the delay interval $\Delta$ as the difference between the last intrinsic contraction of the first ventricle and a set time occurring within the blanking interval,
(2) avoid stimulation of the second ventricle for one cardiac cycle,
(3) determine the current intrinsic ventricular interval RR,
(4) define a new delay interval $\Delta$ from the current intrinsic ventricular interval RR, and
(5) reduce the delay interval $\Delta$ until an intrinsic contraction of the first ventricle is detected.

18. The cardiac stimulation method of claim 17 further including the steps of:
a. altering the delay interval $\Delta$ by an interval $\tau$ for a cardiac cycle,
b. determining any resulting change in the RR interval, and
c. reducing the interventricular delay time VVD if a resulting change in the RR interval occurs.

19. The cardiac stimulation method of claim 17 wherein the set time occurs at the middle of the blanking interval.

20. The cardiac stimulation method of claim 17 wherein if, after generation of the ventricular stimulation pulse is suppressed for one cardiac cycle, no intrinsic contraction of the first ventricle is detected by the ventricular sensing unit, the delay interval $\Delta$ is reduced until an intrinsic contraction of the first ventricle is detected.

* * * * *